United States Patent
Bagby (10) Patent No.: US 7,721,732 B2
(45) Date of Patent: May 25, 2010

(54) RESPIRATORY HEAT EXCHANGER

(75) Inventor: Lee R. Bagby, Arvada, CO (US)

(73) Assignee: QXTEC, Inc., Lakewood, CO (US)

( * ) Notice: Subject to any disclaimer, the term of this patent is extended or adjusted under 35 U.S.C. 154(b) by 0 days.

(21) Appl. No.: 10/405,134

(22) Filed: Apr. 1, 2003

(65) Prior Publication Data

US 2004/0011359 A1 Jan. 22, 2004

Related U.S. Application Data (60) Provisional application No. 60/401,641, filed on Aug. 6, 2002, provisional application No. 60/370,513, filed on Apr. 4, 2002.

(51) Int. Cl.
*A62B 18/08* (2006.01)

(52) U.S. Cl. .............. 128/201.13; 128/205.25; 128/206.13; 128/205.29; 128/201.17; 128/201.25; 128/202.19; 128/206.16; 128/206.17; 128/206.19; 128/206.12; 128/206.28; 128/910

(58) Field of Classification Search ............ 128/205.25, 128/206.13, 205.29, 201.13, 201.17, 201.25, 128/202.19, 206.16, 206.17, 206.19, 206.12, 128/206.28, 910

See application file for complete search history.

(56) References Cited

U.S. PATENT DOCUMENTS

| | | | |
|---|---|---|---|
| 387,843 A | 8/1888 | Baggerly | |
| 2,410,903 A | 11/1946 | Rogge | 128/399 |
| 2,626,343 A | 1/1953 | Fogel et al. | 219/46 |
| 3,249,108 A | 5/1966 | Terman | 128/146 |
| 3,326,214 A | 6/1967 | McCoy | 128/212 |
| 3,333,585 A | 8/1967 | Barghini et al. | 128/212 |
| 3,491,754 A | 1/1970 | Weese | |
| 3,814,094 A * | 6/1974 | De Angelis et al. | 128/201.13 |
| 3,835,853 A | 9/1974 | Turner | 128/212 |
| 3,991,754 A | 11/1976 | Gertzman | |
| 4,037,593 A | 7/1977 | Tate, Jr. | |
| 4,136,691 A | 1/1979 | Ebeling et al. | 128/212 |

(Continued)

FOREIGN PATENT DOCUMENTS

CA 2027353 10/1990

(Continued)

OTHER PUBLICATIONS

U.S. Appl. No. 11/551,570, filed Oct. 20, 2006, Bagby.

(Continued)

*Primary Examiner*—Patricia Bianco
*Assistant Examiner*—Nihir Patel
(74) *Attorney, Agent, or Firm*—Sheridan Ross P.C.

(57) ABSTRACT

A heat exchange module comprising a number of substantially parallel and spaced apart heat exchange elements is provided. One or more surfaces of the heat exchange elements may be coated with a dessicant. The module can be manufactured so that first and second surfaces of the module are curved. The module may be used as part of a face mask or other garment that positions the module within the respiratory air stream of a user. The module may be inserted in a mesh sleeve provided as part of the garment. The module may also be used as part of other forms of clothing that protect the face and in protective helmets, or as part of outdoor or survival equipment.

25 Claims, 8 Drawing Sheets

U.S. PATENT DOCUMENTS

| | | | |
|---|---|---|---|
| 4,150,671 A | 4/1979 | Tiger | 128/212 |
| 4,196,728 A | 4/1980 | Granite | 128/201.13 |
| 4,200,094 A | 4/1980 | Gedeon et al. | 128/201.13 |
| 4,269,183 A | 5/1981 | Hunt | 128/201.13 |
| 4,273,119 A * | 6/1981 | Marchello | 128/201.13 |
| 4,319,567 A | 3/1982 | Magidson | 128/206.19 |
| 4,323,063 A | 4/1982 | Fisichella | |
| 4,325,365 A | 4/1982 | Barbuto | 128/201.13 |
| 4,412,537 A | 11/1983 | Tiger | 128/204.17 |
| 4,432,409 A | 2/1984 | Steele | |
| 4,441,494 A | 4/1984 | Montalbano | 128/204.17 |
| 4,458,679 A | 7/1984 | Ward | 128/201.13 |
| 4,461,292 A | 7/1984 | Montalbano | 128/204.17 |
| 4,473,071 A | 9/1984 | Hunt | 128/201.13 |
| 4,478,215 A | 10/1984 | Hanlon | 128/201.13 |
| 4,601,287 A | 7/1986 | Royce, Jr. | 128/204.17 |
| 4,620,537 A | 11/1986 | Brown | 128/201.13 |
| 4,671,268 A | 6/1987 | Hunt | 128/201.13 |
| 4,682,869 A | 7/1987 | Itoh et al. | |
| 4,683,869 A | 8/1987 | Wilcox | 126/204 |
| 4,768,235 A | 9/1988 | Webster | 2/205 |
| 4,793,343 A | 12/1988 | Cummins, Jr. et al. | 128/204.17 |
| 4,793,383 A | 12/1988 | Gyory et al. | |
| 4,825,474 A | 5/1989 | Edwards | 2/206 |
| 4,829,997 A | 5/1989 | Douwens et al. | 128/201.13 |
| 4,875,520 A | 10/1989 | Steele et al. | 165/10 |
| 4,905,686 A | 3/1990 | Adams | |
| 5,007,114 A | 4/1991 | Numano | |
| 5,010,194 A | 4/1991 | Mueller et al. | |
| 5,058,211 A | 10/1991 | Hanks | 2/206 |
| 5,063,923 A | 11/1991 | Peroni | |
| 5,086,766 A | 2/1992 | Beacham | 128/203.27 |
| 5,320,096 A * | 6/1994 | Hans | 128/205.29 |
| 5,339,653 A | 8/1994 | DeGregoria | |
| 5,401,706 A | 3/1995 | Fischer | |
| 5,433,192 A | 7/1995 | Ebeling | 128/201.13 |
| 5,435,299 A | 7/1995 | Langman | 128/201.13 |
| 5,443,192 A | 8/1995 | Hodges et al. | |
| 5,445,876 A | 8/1995 | Kyricos | 428/283 |
| 5,570,684 A | 11/1996 | Behr | |
| 5,595,173 A | 1/1997 | Dodd, Jr. | |
| 5,617,913 A | 4/1997 | DeGregoria et al. | 165/104.11 |
| 5,701,891 A | 12/1997 | Groenke | |
| 5,701,892 A | 12/1997 | Bledstein | |
| 5,706,802 A | 1/1998 | McCormick | 128/204.17 |
| 5,727,616 A | 3/1998 | Groenke | 165/4 |
| 5,873,256 A | 2/1999 | Denniston | |
| RE36,165 E | 3/1999 | Behr | |
| 5,937,856 A | 8/1999 | Jonasson et al. | |
| 5,937,933 A * | 8/1999 | Steele et al. | 165/10 |
| 5,964,221 A * | 10/1999 | McKenna | 128/205.12 |
| 6,102,037 A | 8/2000 | Koch | |
| 6,196,221 B1 | 3/2001 | McCormick | 128/204.17 |
| 6,244,266 B1 | 6/2001 | Margiotta, Jr. | |
| 6,308,703 B1 | 10/2001 | Alving et al. | |
| 6,319,599 B1 | 11/2001 | Buckley | |
| 6,340,024 B1 | 1/2002 | Brookman et al. | |
| 6,520,181 B2 | 2/2003 | Baumann et al. | |

FOREIGN PATENT DOCUMENTS

FI          895044          10/1989

OTHER PUBLICATIONS

Restriction Requirement for U.S. Appl. No. 11/551,570, mailed Jul. 9, 2009, 5 pages.

* cited by examiner

RESPIRATORY HEAT EXCHANGER

CROSS REFERENCE TO RELATED APPLICATIONS

This application claims the benefit of U.S. Provisional Patent Application Ser. No. 60/401,641, filed Aug. 6, 2002 entitled "DESICCANT-COATED PLASTIC RESPIRATORY HEAT EXCHANGER," and U.S. Provisional Patent Application Ser. No. 60/370,513, filed Apr. 4, 2002, entitled "USE OF DESICCANT-COATED PLASTIC IN RESPIRATORY HEAT EXCHANGER," the entire disclosures of which are incorporated herein by reference.

FIELD OF THE INVENTION

The present invention relates to an apparatus that uses the heat and humidity from exhaled air to warm and humidify inhaled air. A method for producing the apparatus is also provided.

BACKGROUND OF THE INVENTION

A person working at cold temperatures (for example 40° F. or less) under winter conditions or staying outdoors under very cold conditions, e.g., in arctic areas, has to breathe in great amounts of cold, dry air. This is not only unhealthy, but also substantially increases the loss of heat of the person as the body tends to warm up the inhalation air to the temperature of the body, and this amount of heat is removed from the body with the exhalation air. In addition, dry inhalation air has a disadvantageous effect on the normal moistness of the mucous membranes of the respiratory passages.

The detrimental effects of breathing cold air, particularly for people with medical problems such as cardiac conditions, angina, and asthma, and the benefits of heating inhaled air, have been recognized for many decades. Respiratory heat exchangers are intended to transfer heat, water vapor, or both between incoming and outgoing ventilation airstreams so as to keep the user warm. Through natural breathing of the wearer, the airstream is alternately directed through the entire exchange device first in one direction and then in the opposite direction.

Known heat transfer devices have been described as falling into one of three categories: (1) those designed primarily for the exchange of sensible heat; (2) those designed primarily for the exchange of latent heat; and (3) those designed to exchange both sensible and latent heat (the so-called "enthalpy exchangers"). To maximize the benefit of respiratory heat exchangers, it is desirable to choose a heat exchange material that is capable of providing high sensible and latent heat exchange efficiencies. Devices that heat and humidify inhaled air with exhaled air by passing the air though an exchanger fabricated from either foil, a nonwoven resilient porous fibrous organic polymeric material, a foraminous heat conductive material, or a continuous strip of wire netting wound helically are known. Other such devices provide a strip of thermally insulative material retained within a bandanna and positioned adjacent the mouth of a user. The use of metal, wool, uncoated metal strips, certain coated Kraft papers, and other fibrous cellulose materials tend to be unsatisfactory because the latent heat exchange efficiency of these materials is relatively poor, as compared to the sensible heat exchange efficiency. Inhaled air has been heated with electrical heating elements and with heated water. Inhaled air has also been heated by devices that obtain heat from portions of the human body rather than external power sources.

Widespread use of a device for warming air that is breathed in requires that the device be relatively small, lightweight, and inexpensive. Currently, there is widespread use of devices that cover the face in cold weather. Some such devices incorporate a heat exchange respiratory device. Available devices, however, are either unwieldy, very heavy, very expensive to manufacture, or not durable. In addition, none provide for the most efficient use of a heat-exchanging medium. Therefore, it can be appreciated that there exists a continuing need for a new and improved heat exchanger that can be used for maintaining warmth in a wearer. In this regard, the present invention substantially fulfills this need.

SUMMARY OF THE INVENTION

The present invention is directed to a method and apparatus for providing heated and humidified respiratory air to a user. In general, a heat exchange module is formed from a plurality of heat exchange elements or surfaces that are substantially parallel to and spaced apart from one another. The heat exchange module accordingly allows respiratory air to pass across the surface of the heat exchange elements. Air that is exhaled across the surface area of the heat exchange elements tends to heat and humidify those strips. Relatively cold, dry air that is inhaled across the heat exchange elements is heated and humidified using the heat and humidity imparted to the elements during a previous exhalation step.

In accordance with an embodiment of the present invention, the heat exchange elements are substantially planar and are formed from a rigid plastic material. Some or all of the heat exchange elements may comprise or may be coated with a desiccant. In accordance with an embodiment of the present invention, the heat exchange elements alternate between desiccant-coated and non-desiccant-coated heat exchange elements. In accordance with a further embodiment of the present invention, the heat exchange elements alternate between heat exchange elements having protrusions formed thereon and heat exchange elements that are substantially smooth. The heat exchange elements may be interconnected to one another at two opposing edges of the module using an interconnecting member comprising a layer of glue, or an additional piece of material combined with glue. In accordance with a further embodiment of the present invention, the heat exchange elements of a module may be interconnected to one another by an interconnecting member comprising a frame defining the periphery of the module.

The present invention additionally includes methods of forming heat exchange modules in accordance with the present invention. According to one such method, heat exchange elements are formed from plastic strips arranged in a jig having a curved support surface such that the strips are generally parallel to one another. In addition, each strip is spaced apart from an adjacent strip. The spacing of the strips may be accomplished by using strips that have protrusions formed thereon. In accordance with a further embodiment of the present invention, the spacing is accomplished by alternating strips having protrusions formed thereon and strips that are substantially smooth. In accordance with still another embodiment, at least some of the plastic strips include a desiccant. The method further includes using a hot knife to form the periphery of an individual heat exchange module. The use of a hot knife tends to fuse the edges of the heat exchange elements formed from the plastic strips to one another, at least temporarily. The elements forming the module may then be removed from the jig, and more permanently secured using glue and/or by placing the heat exchange elements of the module within a frame.

The present invention additionally includes a method for providing heated and humidified air to a user. According to an embodiment of the method, a heat exchange module formed from substantially parallel heat exchange elements, at least some of which are desiccant-coated, is placed across at least a portion of an air stream of a user. In accordance with another embodiment, a heat exchange module comprising a plurality of heat exchange elements and having a curved surface to facilitate positioning the module adjacent the nose and/or mouth of the user is placed across at least a portion of an air stream of a user. In accordance with an embodiment of the present invention, a heat exchange module may be positioned in front of the nose and/or mouth of the user by incorporating the module within a garment, such as a face mask, balaclava, helmet, or jacket collar.

Additional advantages of the present invention will become readily apparent from the following discussion, particularly when taken together with the accompanying drawings.

DETAILED DESCRIPTION

The device described herein comprises heat exchange modules suitable for use in heating and humidifying air in connection with animal respiratory functions. Methods of manufacturing such modules and of heating respiratory air are also described. A heat exchange module may, in accordance with the present invention, be used as part of a face mask or on other forms of clothing currently known that protect the face, or incorporated into other garments, outdoor equipment and survival equipment.

Figure 1:
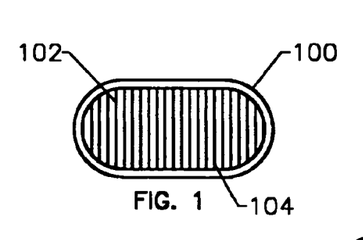
FIG. 1 is a front view of a heat exchange module in accordance with an embodiment of the present invention.

With reference now to FIG. 1, a heat exchange module in accordance with an embodiment of the present invention is illustrated in plan view. In general, the heat exchange module 100 includes a heat exchange material or medium 102 having a matrix of heat exchange elements 104 at least some of which have a dry desiccant on a surface thereof. In accordance with an embodiment of the present invention, the quantity of dry desiccant affixed to each strip is selected so that the sensible and latent heat transfer efficiencies of the material 102 are relatively high and approximately equal. The matrix of heat exchange elements 104 provide spaces between adjacent elements to allow for the passage of air therebetween.

Figure 2:
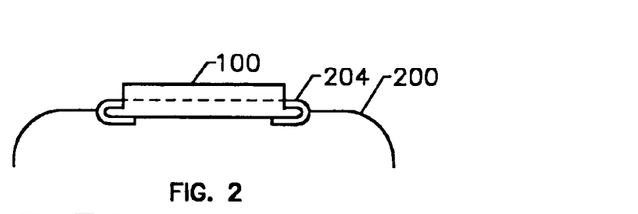
FIG. 2 is a cross-section of a heat exchange module in accordance with an embodiment of the present invention and the attachment of the module to a garment.

With reference now to FIG. 2, a heat exchange module 100 is illustrated in plan view, in combination with a garment 200. The module 100 may be attached to the garment 200 along an attachment seam 204 comprising glue, an elastic sleeve, or a seam formed by fusing the module 100 to the garment 200 or vice versa.

Figure 3:
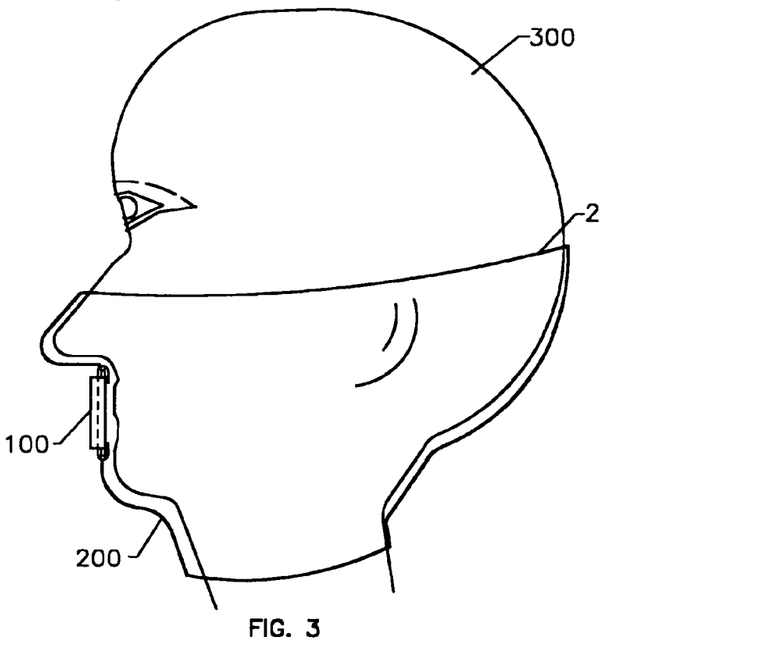
FIG. 3 illustrates a garment with a module in accordance with an embodiment of the present invention attached as worn by a person.

With reference now to FIG. 3, the garment 200 incorporating the module 100 is shown as worn by a person 300. In general, the module 100 is positioned such that all or a substantial portion of the person's breath is passed through the module 100. As breath is exhaled through the module 100, heat and moisture are removed. In particular, the desiccant of the module 100 removes water vapor from the exhaled air, which in turn removes heat from the exhaled air, particularly as the water in the exhaled air undergoes a phase change from a vapor to a liquid. As air is inhaled through the module 100, heat and water removed from exhaled air are added to the relatively cold, dry air being inhaled as that cold, dry air passes through the module 100. Accordingly, the air inhaled by the wearer is heated and humidified.

Figure 4:
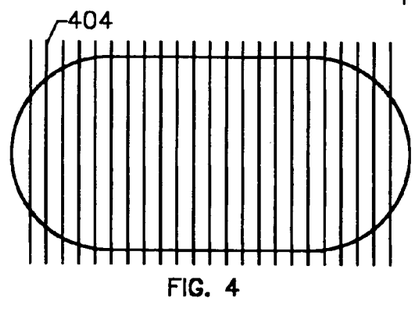
FIG. 4 is a plan view of the shape of a module in accordance with an embodiment of the present invention while being cut from a spool of heat exchange material.

The module 100 may be cut from sheets of the matrix material. For example, in FIG. 4, the outline of a module 100 prior to being cut from a sheet 400 comprising a matrix of plastic strips 404 is illustrated.

Figure 5:
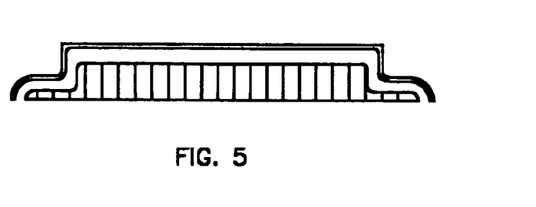
FIG. 5 is a cross-section of a module in accordance with an embodiment of the present invention and a die.

In FIG. 5, a die 500 that may be used to form a module 100 in a single step is illustrated. The die 500 is heated by supplying electrical current through the wires 504. In general, the die 500 is pressed against the sheet 400 to define the perimeter of a module 100. In addition, the die may define shoulders 512 to facilitate interconnecting the module 100 to a garment 200. Heat provided at least along the cutting edge 508 of the die 500 cuts the module 100 from the surrounding sheet of material 400, and fuses the edges of the thus formed module 100. Accordingly, the module 100 may be formed in a single step.

Figure 6:
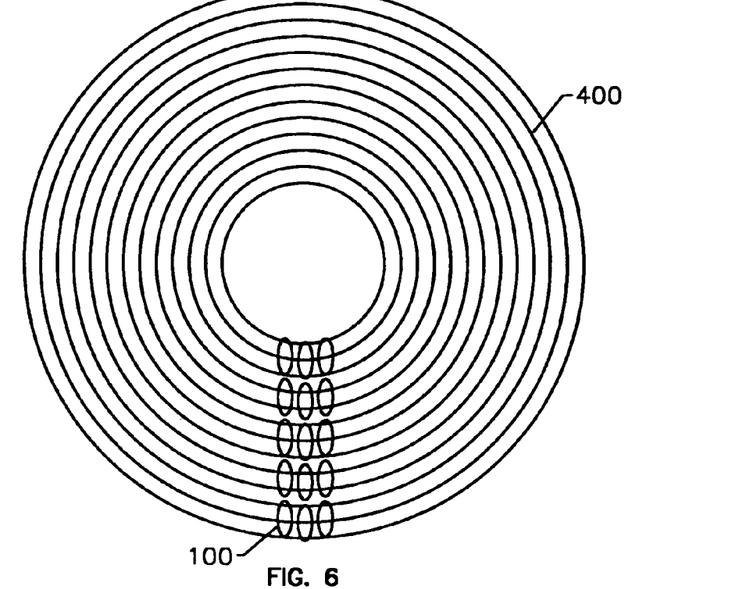
FIG. 6 is a plan view of a spool of desiccant-coated plastic heat medium from which heat exchange modules in accordance with the present invention may be formed.
Figure 7:
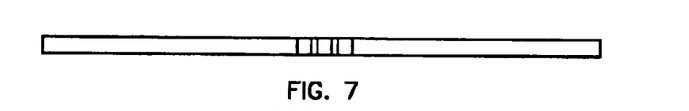
FIG. 7 is an elevation of the spool of FIG. 6.

With reference now to FIG. 6, a sheet 400 in the form of a spool of matrix material is illustrated. Also shown are the outlines of a plurality of modules 100, illustrating that a number of such modules may be formed from a single sheet or spool 400 of material. In FIG. 7, the sheet or spool 400 of FIG. 6 is shown in plan view.

The material comprising the plastic elements 104 of the matrix of the module 100 may comprise strips 404 of rigid plastic having a desiccant deposited on at least one surface thereof. The desiccant may be in the form of finely comminuted particles placed on a plastic element. The plastic strips 404 from which the elements 104 are formed may be wound, laid parallel to one another, or folded to create the spool or sheet 400. In accordance with another embodiment of the present invention, multiple plastic strips 404 may be laid parallel to one another, forming a rectangular sheet 400 (see, e.g., FIG. 4). Suitable material is available from Airxchange, Inc. of Rockland, Mass., and the composition and manufacture of such material is described in U.S. Pat. No. 4,875,520, the entire disclosure of which is hereby incorporated by reference.

The shape of the die 500 can be arranged such that later attachment of the module 100 to the garment is easily accomplished. The type and quantity of desiccant used, the area within the perimeter of the module 100, and the thickness of the module 100 are a function of the use of the user or wearer. For example, an active athlete would want relatively little effectiveness to facilitate the natural heat rejection from the body required for strenuous exercise, while a security guard standing for hours in an extremely cold environment requires maximum heat exchange efficiency. Furthermore, different people breathe different volumes per breath. The optimum module 100 thickness, the area within the perimeter of the module 100, and desiccant selection should therefore be varied according to individual requirements. In general, the thickness of a module 100 may be determined by the width of the plastic strip or strips 404 used to form the spool or sheet 400. The area within the perimeter of the module 100 may be determined by the size and shape of the die 500 used to form the module 100. In accordance with an embodiment of the present invention, a general purpose module 100 is formed from strips of plastic, and has a thickness (i.e. a strip 404 width) of ¾", a maximum width of 2½", and a maximum height of 1½" to provide a total heat exchange surface area of about 100 in$^2$.

Once the heat exchange module 100 is made, it may then be attached to a garment or holding device 200. An exemplary garment for this application is a face mask. An appropriately shaped hole (for example an oval), generally conforming to the shape of the perimeter of the module 100, is cut into the mask just under the nose position and in front of the mouth. The attachment seam is labeled number 204 in FIG. 2. The seam can be glue, an elastic sleeve, or it can be fused to the module 100 using heat only if the garment is made of fleece or other synthetic material. Once the module 100 is in place, the garment is worn exactly as it was intended prior to the addition of the module 100.

If the seam 204 is an elastic sleeve, the module 100 can be easily removed for cleaning or replacement. Accordingly, different modules 100 could be used to provide the optimum heat exchange capability for the immediate use.

Similarly, the module 100 can be attached to a hood, balaclava, or other well-known garment used to protect the face from the cold. The module 100 may also be placed into the front of a ski, motorcycle, snowmobile, or other helmet with a facial covering. A hole is cut in the front of the mouth, and the module 100 is placed into the hole and attached. The shape of the die 500 could be altered to match the shape of the helmet and the hole. In accordance with still other embodiments, the module 100 is incorporated into outdoor equipment comprising other than head wear or a face mask, such as a jacket, sleeping bag or tent. The module 100 may also be incorporated into survival gear, including underwater or firefighting breathing apparatuses.

Figures 8, 9:
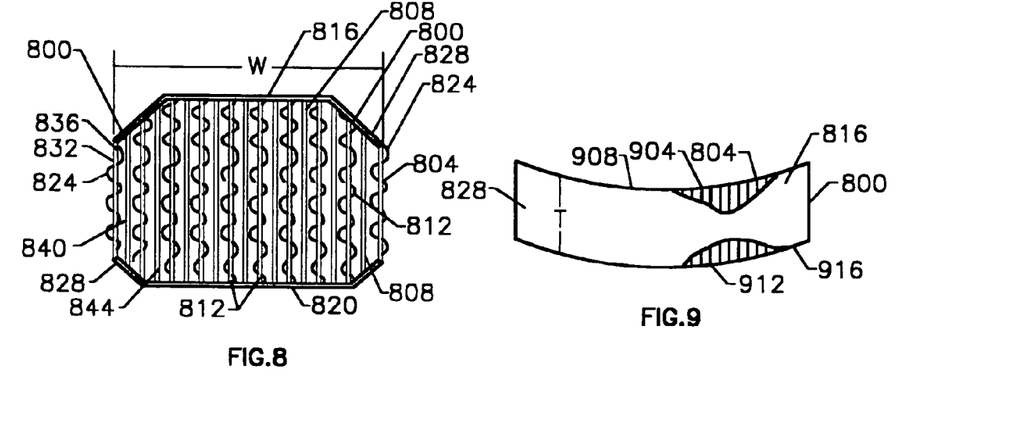
FIG. 8 is a front view of a heat exchange module in accordance with another embodiment of the present invention.
FIG. 9 is a top view of the heat exchange module of FIG. 8.

With reference now to FIGS. 8 and 9, a heat exchange module 800 in accordance with another embodiment of the present invention is shown. In FIG. 8, the heat exchange module 800 is shown in a front or elevation view. FIG. 9 shows the heat exchange module 800 in a top view. As shown in FIG. 8, the heat exchange module 800 includes a number of generally parallel heat exchange elements in the form of substantially planar pieces of heat exchange material 804. In the embodiment illustrated in FIG. 8, the pieces of material 804 alternate between desiccant coated plastic elements 808 and uncoated plastic element 812. The provision of desiccant coated plastic elements 808 improves the heat exchange efficiency of the heat exchange module 800 by removing water vapor from exhaled air. The provision of uncoated plastic elements 812 improves the adherence of the elements 808, 812 to one another at the first 816 and second 820 edges of the module 800. However, such alteration between types of elements 804 is not required. For example, all of the heat exchange elements 804 may be desiccant-coated 808. The heat exchange elements 804 may be formed from substantially rigid plastic, so that the spacing between elements 804 is maintained and so that the module 800 generally maintains its shape, but can also flex without breaking.

In the embodiment of a heat exchange module 800 illustrated in FIG. 8, the uncoated plastic elements 812 feature protrusions 824 on the first 832 and second 836 substantially planar side surfaces of the uncoated plastic elements 812, while the first 840 and second 844 side surfaces of the desiccant coated plastic elements 808 are substantially smooth. The protrusions 824 help ensure that a void space is maintained between adjacent elements 808, 812. The protrusions 824 may be formed such that a protrusion 824 from the first side surface 832 of a plastic elements 812 appears as a dimple on the second side surface 836. Although in the embodiment illustrated in FIG. 8 the protrusions 824 are formed in the uncoated plastic elements 812, such is not necessarily the case. For example, protrusions 824 may be formed in desiccant coated plastic elements 808 instead of or in addition to being formed in uncoated elements 812. At first 816 and second 820 edges of the heat exchange module 800, the elements 808, 812, and in particular the uncoated plastic elements 812, partially melt when the module 800 is cut from a matrix of heat exchange material to form an integral heat exchange module 800. In order to further secure the elements 808, 812, layers of glue 828 may be deposited. In accordance with an embodiment of the present invention, the layers of glue 828 are applied using a hot glue gun, as will be described in greater detail below.

As shown in FIG. 9, the heat exchange module 800 is curved, to better conform to the face of a user. In particular, the curve of the heat exchange module 800 improves the comfort and efficiency of the heat exchange module 800. As seen in FIG. 9, a first edge 904 of the elements 804 forms a first (concave) curved surface 908 and a second edge 912 of the elements 804 forms a second (convex) curved surface 916.

Figure 10A:
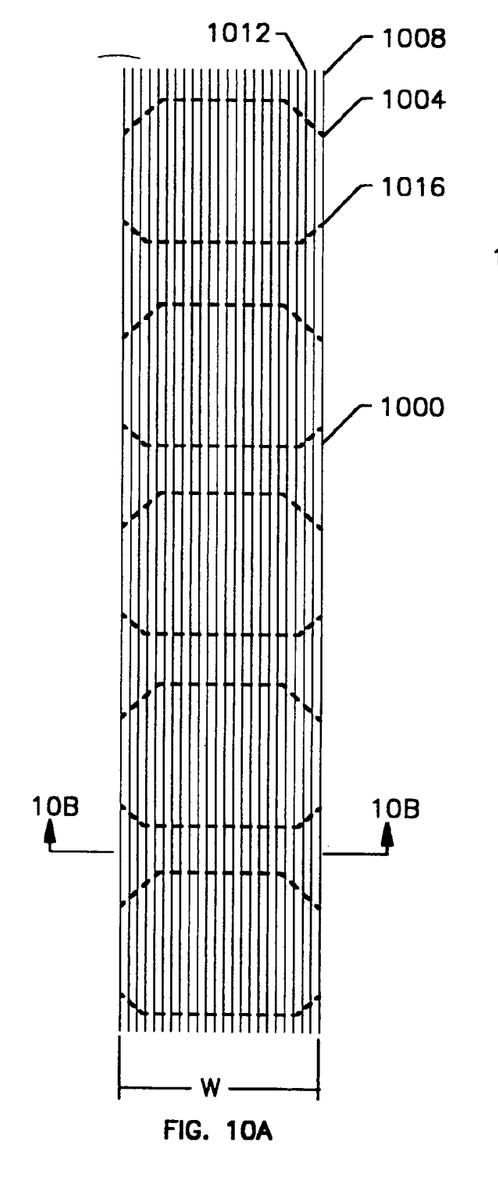
FIG. 10A is a plan view of a collection of strips of material forming a sheet from which a heat exchange module in accordance with an embodiment of the present invention may be formed.
Figure 10B:
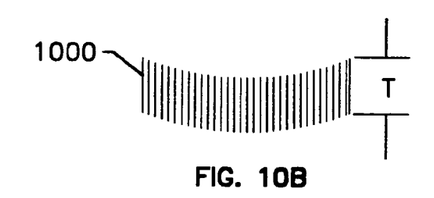
FIG. 10B is a cross-sectional view of the sheet of FIG. 10A taken along line 10B-10B.

With reference now to FIG. 1A, a heat exchange matrix or sheet 1000 comprising a plurality of generally parallel plastic strips 1004 is shown in plan view. The longitudinal edges of the plastic strips 1004 are visible in FIG. 10A. Also shown in FIG. 10A are the outlines 1016 of heat exchange modules 800 that may be formed from the matrix 1000. FIG. 10B illustrates a cross-section of the heat exchange matrix 1000 along line 10B-10B of FIG. 10A, and in particular shows that the matrix 1000 may be formed with or placed in a curved configuration, at least when the heat exchange modules 800 are formed. In accordance with an embodiment of the present invention, the plastic strips 1004 have a width (dimension "T" in FIGS. 9 and 10B) of from about ¼ inch to about 1 inch. Furthermore, the plastic strips 1004 may alternate between uncoated plastic strips 1012 and desiccant coated plastic strips 1008. One or both of the plastic strips 1008 or 1012 may be provided with protrusions 824 to maintain a separation between adjacent plastic strips 804. The plastic strips 1004 may comprise a substantially rigid material, allowing a heat exchange module 800 formed from the matrix 1000 to maintain its shape and the spacing between adjacent heat exchange elements 804.

Figure 11:
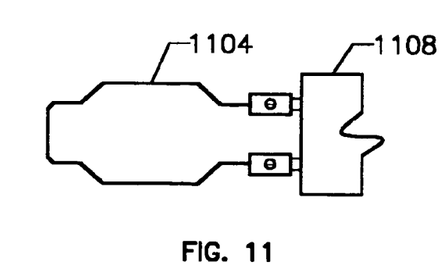
FIG. 11 is a top view of a hot knife blade for forming a heat exchange module in accordance with an embodiment of the present invention.

With reference now to FIG. 11, the blade 1104 of a hot knife 1108 (shown in partial view in FIG. 11) is depicted in plan view. As can be appreciated by a comparison of the hot knife blade 1104 outline to the outline of the heat exchange module shown at FIG. 8, the hot knife blade 1104 generally defines the upper 816 and lower 820 edges of the heat exchange module 800. Furthermore, and with reference to FIG. 10, it can be appreciated that the number of plastic strips 1004 laid alongside one another determines the width of the heat exchange module 800 (dimension "W" in FIGS. 8, 10 and 12).

Figure 12:
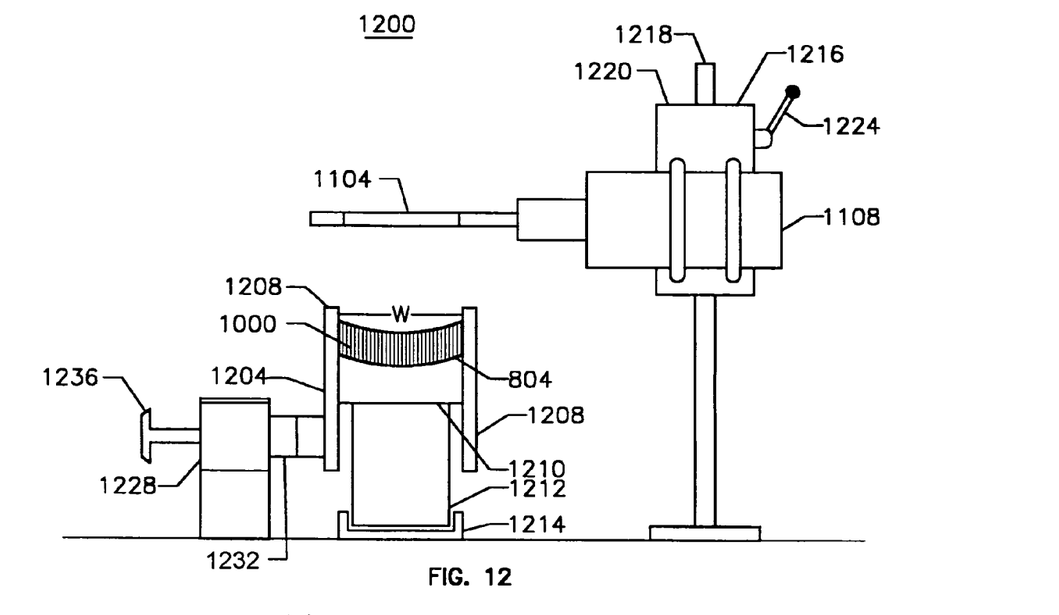
FIG. 12 is an elevation of an apparatus for forming heat exchange modules in accordance with an embodiment of the present invention.

With reference now to FIG. 12, an apparatus 1200 for repeatably forming heat exchange modules 800 is shown in elevation. In general, the apparatus 1200 includes a jig 1204 for holding a matrix 1000 formed from a number of plastic strips 1004 from which the heat exchange elements 804 of heat exchange modules 800 are formed. In general, the distance between the side plates 1208 of the jig 1204 is equal to the width "W" of the heat exchange module 800. The jig 1204 includes ribs 1210 interconnecting the side plates 1208. The ribs 1210 have a curved upper surface, which provides the curve in the module 800 seen in FIG. 9, and the curve in the matrix 1000 seen in FIG. 10B. The jig 1204 further includes a longitudinal rail 1212 that can slide within a channel 1214 in a direction perpendicular to the width W of the matrix 1000. An indexer 1228 may be used to control the longitudinal position of the jig 1204. In particular, a bolt 1232 of the indexer 1228 may engage slots 1408 (see FIG. 14) on the side plate 1208 of the jig 1204 adjacent the indexer 1228 to ensure that the jig 1204 is in the desired position relative to the hot knife blade 1104. A handle 1236 may be provided to allow an operator to conveniently pull the bolt 1232 clear of the indexing slot 1408 when the position of the jig 1204 is being changed.

The apparatus 1200 additionally includes the hot knife 1108. The hot knife 1108 is mounted to a vertical press 1216 that includes a vertical post 1218 and a traveling assembly 1220. The traveling assembly 1220 may be interconnected to the vertical post 1218 such that the traveling assembly 1220 is selectively moveable in a vertical direction (i.e. along the axis of the vertical post 1218), and such that movement in other directions is substantially prohibited. The vertical press 1216 may further include a handle 1224 to allow an operator to control the vertical position of the traveling assembly 1220, and in particular the position of the blade 1104 of the hot knife 1108 relative to the matrix or sheet 1006.

Figure 13:
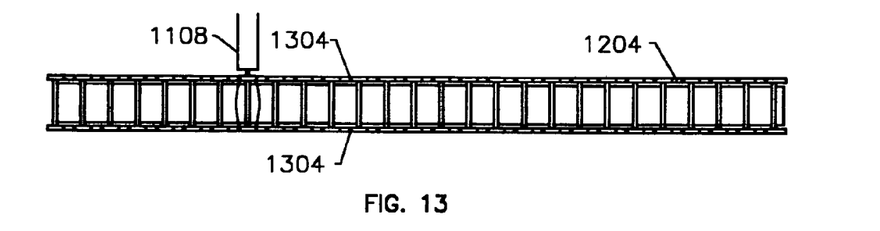
FIG. 13 is a top view of a jig and hot knife for forming heat exchange modules in accordance with an embodiment of the present invention.

With reference now to FIG. 13, the jig 1204 and hot knife 1108 are shown in plan view. As shown in FIG. 13, the jig 1204 includes a plurality of slots 1304. The slots 1304 are spaced to allow the hot knife blade 1104 to cut the matrix 1000 of plastic strips 1004 held in the jig 1204 when heat exchange modules 800 are being formed. In addition, every other one of the slots 1304 in the side plate 1208 adjacent the indexer 1228 functions as an indexing slot 1408 (see FIG. 14) that can be selectively engaged by the bolt 1232 of the indexer 1228 (FIG. 12).

Figure 14:
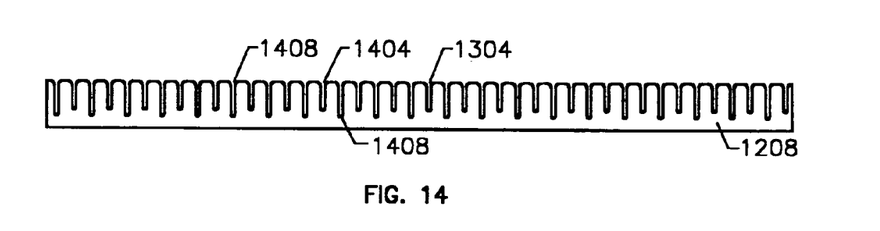
FIG. 14 is an elevation of a jig for forming heat exchange modules in accordance with an embodiment of the present invention.

With reference now to FIG. 14, a side wall 1208 that is positioned adjacent the indexer 1228 of a jig 1204 in accordance with an embodiment of the present invention is shown. FIG. 14 shows that the slots 1204 alternate between relatively short slots 1404 and indexing slots 1408. The indexing slots 1408 are deeper, to allow the bolt 1232 of the indexer 1228 to engage them.

Figure 15:
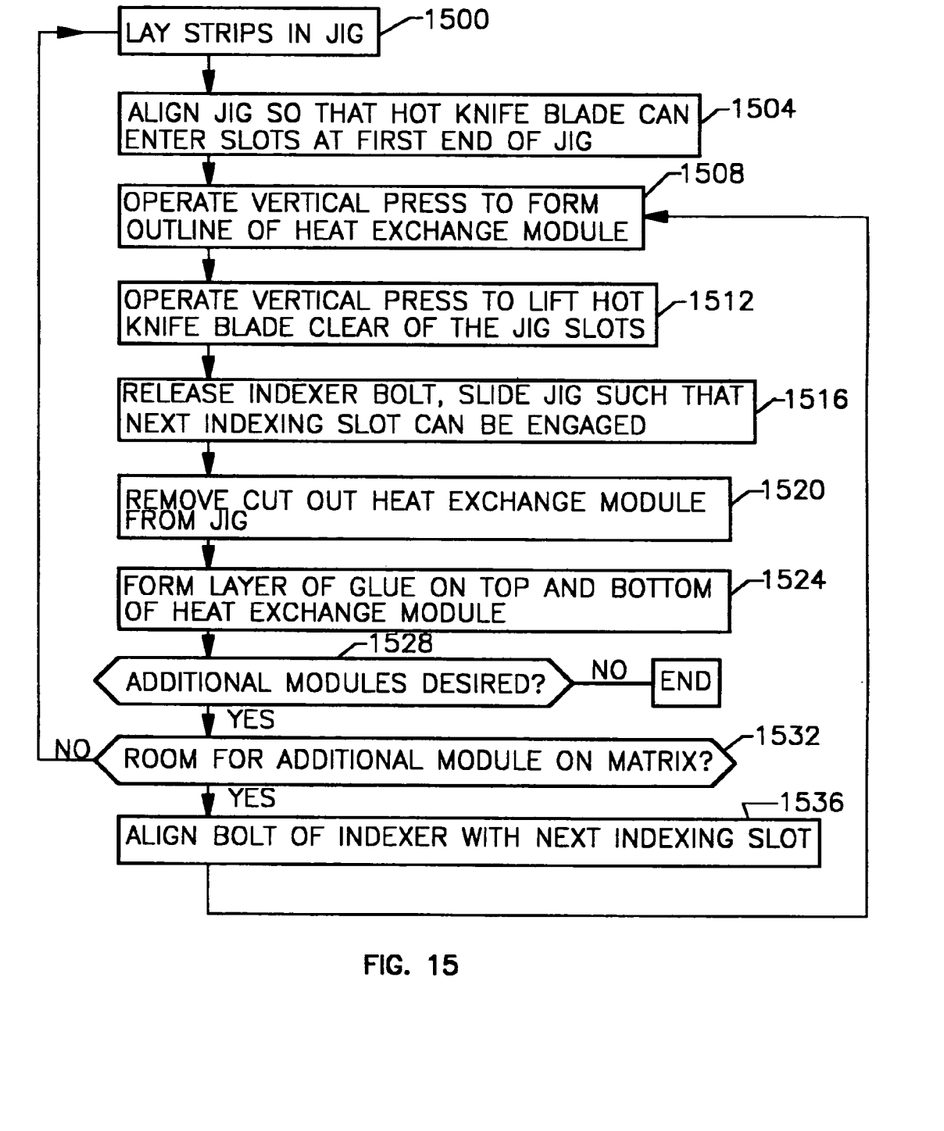
FIG. 15 is a flow chart depicting the manufacture of a heat exchange module in accordance with an embodiment of the present invention.

With reference now to FIG. 15, steps taken in connection with the manufacture of a curved heat exchange module 800 in accordance with an embodiment of the present invention are shown. Initially, at step 1500, plastic strips 1004 are laid in the jig 1204, such that the strips are substantially parallel to one another, and such that they form a matrix 1000 in the form of a sheet having a width about equal to the width W between the side plates 1208 of the jig 1204. Furthermore, the strips 1004 are laid in the jig 1204 such that they are in contact with the curved top surface of the ribs 1210 of the jig 1204. In accordance with an embodiment of the present invention, the strips 1004 are packaged by a supplier such that the strips 1004 are parallel to one another, and thus can be lifted out from the packaging in matrices having the appropriate width W. Furthermore, where the strips 1004 comprise different materials or types, such as alternating between uncoated 1008 and desiccant coated 1012 strips, the alternating or other pattern can be established as the strips are supplied and packaged. Alternatively, different strips 1004 can be individually laid into the jig 1204 to obtain the desired width and pattern of strip 1004 types (e.g., a pattern alternating between uncoated 1008 and desiccant coated 1012 strips 1004).

At step 1504, the jig 1204 is positioned such that the slots 1304 at one end of the jig 1204 are beneath the blade 1104 of the hot knife 1108. In particular, the jig 1204 is aligned such that the bolt 1232 of the indexer 1228 is engaged with the indexing slot 1408 that allows the hot knife blade 1104 to travel within the pair of slots 1304 at the first end of the jig 1204. Generally, the plastic strips 1004 are in lengths that are about equal to the length of the jig 1204. As can be appreciated, however, shorter or longer lengths may be used.

After the jig 1204 has been aligned, the handle 1224 of the vertical press 1216 may be operated such that the blade 1104 of the hot knife 1108 can travel in the slots 1304 of the jig 1204, to cut the strips 1004 in the form of a heat exchange module 800 (step 1508). As the blade 1104 of the hot knife 1108 passes through the matrix 1000 of plastic strips 1004, the strips are cut to form a heat exchange component comprising heat exchange elements 804 in the outline of a heat exchange module 800. In addition, because the hot knife blade 1104 cuts by melting the plastic strips 1004, the plastic strips 1004 are at least partially fused at the first 816 and second 820 edges of the heat exchange module 800. Of course, if the hot knife 1108 has not been on long enough to sufficiently heat the blade 1104, operation of the vertical press 1216 should be delayed until the blade 1104 is sufficiently hot to make a clean cut.

After the cut has been made, the handle 1224 of the vertical press 1216 may be operated to raise the hot knife blade 1104 clear of the jig slots 1304 (step 1512). The handle 1236 of the indexer 1228 may then be operated (e.g., pulled against the force of a spring biasing the bolt 1232 against the side wall 1208 of the jig 1204) to release the bolt 1232 from the indexing slot 1408, and the jig 1208 may be moved relative to the channel 1214, such that the bolt 1232 may engage the next indexing slot 1408 (step 1516). Next, the heat exchange module 800 cut from the matrix 1000 of plastic strips 1004 at step 1508 may be removed from the jig (step 1520). Following removal of the cut out heat exchange module 800 from the jig 1204, a glue layer 828 may be applied to the first 816 and second 820 edges of the heat exchange module 800, to complete formation of the heat exchange module 800 (step 1524). In accordance with an embodiment of the present invention, the glue layers 828 are formed on the heat exchange module 800 using a hot glue gun. The hot glue gun may feature a tip having a width that is about equal to the thickness T of the heat exchange module 800 to improve the efficiency with which the glue 828 can be applied.

In accordance with another embodiment of the present invention, strips of fabric or other material may be glued to the first 816 and second 820 edges of the heat exchange module 800. As can be appreciated, the material may be patterned so that the contours of the first 816 and second 820 edges of the heat exchange module 800 are followed.

At step 1528, a determination is made as to whether the formation of additional heat exchange modules 800 is desired. If no additional modules are desired, the process ends. If additional modules are desired, a determination is made as to whether there is room on the matrix of strips 1004 forcing the material 1000 to form an additional heat exchange module 800 (step 1532). In general, the length of the strips 1004 will be about equal to the length of the jig 1204. Accordingly, if the indexer bolt 1232 is not engaged with the last indexing slot 1408 (i.e. the indexing slot 1408 at the second end of the jig 1204), the jig is aligned such that the bolt 1232 of the indexer 1228 can engage the next indexing slot (step 1536). The process may then return to step 1508. If there is no room for an additional module 800 on the matrix, the process may return to step 1500.

Figure 16:
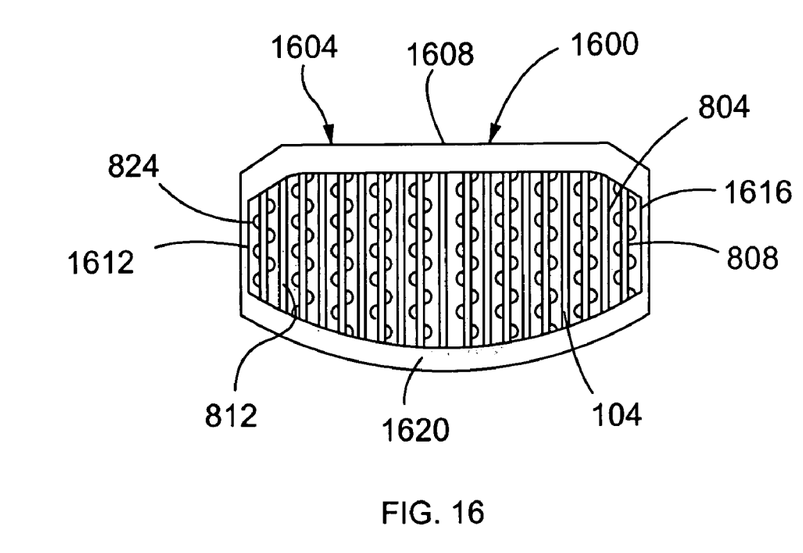
FIG. 16 is an elevation of a heat exchange module in accordance with another embodiment of the present invention.

FIG. 16 is an elevation of a heat exchange module 1600 in accordance with another embodiment of the present invention. In general, the heat exchange module 1600 comprises a plurality of heat exchange elements 804. The elements 804 alternate between desiccant-coated plastic elements 808 and uncoated plastic elements 812. The elements 804 can be formed from a plastic that is substantially rigid, such that no support structure is required in order to maintain the elements 804 spaced apart from one another and in a substantially planar shape. As shown in FIG. 16, the desiccant-coated plastic elements 808 may include dimples or protrusions 824 to space the elements 808 from adjacent elements 808 or 812. The embodiment of the heat exchange module 1600 illustrated in FIG. 16 also includes a frame 1604 having top 1608, side 1612 and 1616, and bottom 1620 portions. In accordance with an embodiment of the present invention, the frame 1604 is formed from a molded plastic material. The frame 1604 may be provided in place of or in addition to a layer of glue placed about the periphery of the module (see, e.g., module 800 in FIG. 8 and glue layer 828). In accordance with an embodiment of the present invention, the individual elements 804 are held or caged by opposite sides of the frame 1604. For example, the embodiment illustrated in FIG. 16 includes a frame 1604 with a top 1608 and a bottom 1620 between which the elements 804 are caged. Accordingly, the frame 1604 can facilitate the provision of a module 1600 that is unitary and durable.

Figure 17:
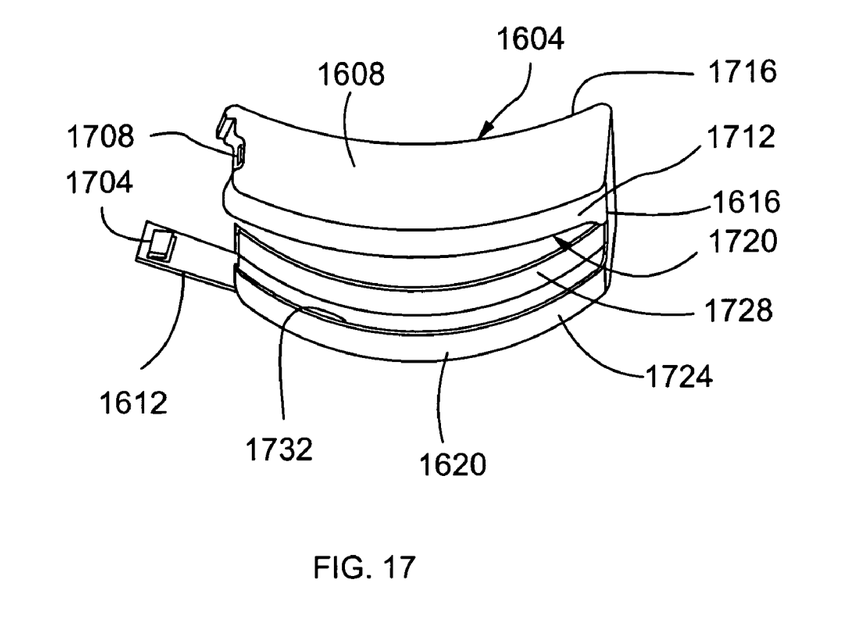
FIG. 17 is a perspective view of a frame for a heat exchange module in accordance with an embodiment of the present invention.

With reference now to FIG. 17, a frame 1604 in accordance with an embodiment of the present invention is illustrated. As seen in FIG. 17, the frame 1604 may be formed from a single piece of molded material. Furthermore, a first side 1612 of the frame 1604 may include a latch member 1704 that is engagingly received by a hole 1708 formed in the top 1608 when the frame 1604 is in position around the plastic strips 104 of the module 1600. In accordance with an embodiment of the present invention, the latch member 1624 and receiving hole 1628 are configured such that the side 1612 is not easily disengaged from the top 1608 after the latch 1624 has been secured in the receiving hole 1628.

The top 1608 may include front 1712 and back walls 1716 to form a top channel 1720. Similarly, the bottom 1620 may include front 1724 and back 1728 to form a bottom channel 1732. The top 1720 and bottom 1732, in combination with the sides 1612 and 1616, may thus function to cage the elements 804 of the module 1600. Furthermore, the spacing between adjacent elements 804 that allows respiratory air to pass across the surfaces of the elements 104 is maintained by the protrusions 824.

Figure 18:
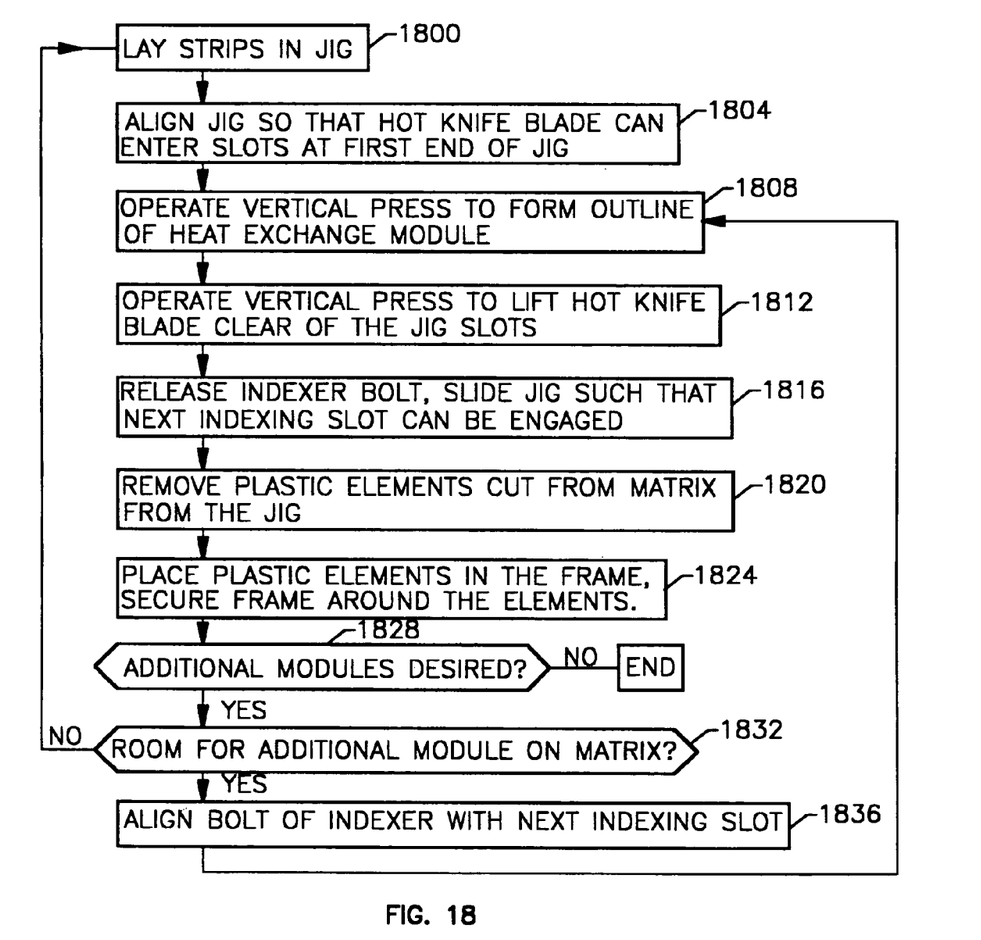
FIG. 18 is a flow chart depicting the manufacture of a heat exchange module in accordance with another embodiment of the present invention.

With reference now to FIG. 18, the manufacture of a curved heat exchange module 1600 having a frame 1604 in accordance with an embodiment of the present invention is illustrated. Initially, at step 1800, plastic strips 1004 are laid in the jig 1204, such that the strips 1004 are substantially parallel to one another, and such that they form a matrix 1000 having a width about equal to the width W between the side plates 1208 of the jig 1204. Furthermore, the strips 1004 are laid in the jig 1204 such that they are in contact the curved top surface of the ribs 1210 of the jig 1204.

At step 1804, the jig 1204 is positioned such that the slots 1304 are at one end of the jig 1204 beneath the blade 1104 of the hot knife 1108. Accordingly, step 1704 is similar to step 1504 in FIG. 15.

As in step 1508 of FIG. 15, at step 1808, the vertical, press 1216 is operated to cause the blade 1104 of the hot knife 1108 to travel in the slots 1304 of the jig 1204, and cut the strips 1004 such that a heat exchange component having heat exchange elements cut in the outline of the frame 1604 in which the elements 804 will be positioned in the completed module 1600 is formed.

The handle 1224 of the vertical press 1216 is then operated to raise the hot knife blade 1104 clear of the jig slots 1304 (step 1812). At step 1816, the indexer bolt 1232 is disengaged from the indexing slot 1408, and the jig 1208 moved to engage the next indexing slot 1408. The heat exchange elements 804 that have been cut from the matrix 1000 by the hot knife 1108 are then removed from the jig (step 1820). At step 1824, the plastic elements 804 that have been cut from the matrix 1000 are placed within the frame 1604, and the frame 1604 is secured about the elements 804. For example, the latch member 1704 is engaged with the hole 1708, completing the heat exchange module 1600. In accordance with an embodiment of the present invention, the side 1612 may be glued or fused to the top 1608, in addition to or in place of a latch arrangement.

At step 1828, a determination is made as to whether additional heat exchange modules 1600 are desired. If no additional modules are desired, the process ends. If additional modules are desired, a determination is made as to whether there is sufficient area remaining on the matrix 1000 to form an additional module 1600 (step 1832). If there is not sufficient area, the process returns to step 1800. If sufficient surface area remains, the bolt 1232 is aligned with the next indexing slot 1408 (step 1836), and the process returns to step 1808.

Figure 19:
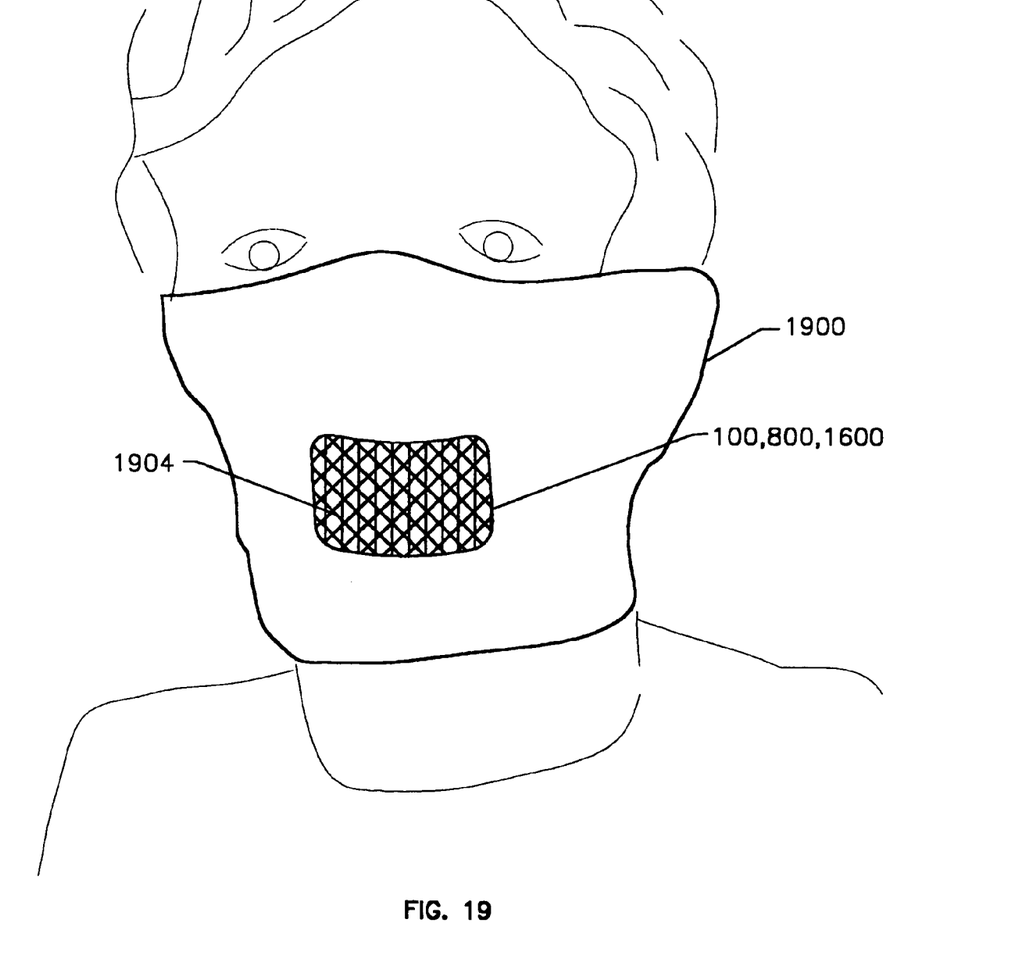
FIG. 19 illustrates a garment incorporating a heat exchange module in accordance with an embodiment of the present invention as worn by a user.

With reference now to FIG. 19, a garment 1900 incorporating a heat exchange module 100, 800 or 1600 in accordance with an embodiment of the present invention is shown. The garment 1900 generally includes a mesh pocket 1904 for receiving the heat exchange module 100, 800 or 1600. The provision of a mesh pocket 1904 allows inhaled and exhaled air to freely pass through the heat exchange module 100, 800 or 1600. Furthermore, by providing a pocket 1804 having at least one open edge, the heat exchange module 100, 800 or 1600 can be placed in or removed from the garment 1800 as desired by the user. The open edge of the pocket 1804 may be provided with an elastic band 1808 to secure the heat exchange module 100, 800 or 1600 within the pocket 1804.

A heat exchange module 100, 800 or 1600 in accordance with embodiments of the present invention provides relatively low resistance to flow while providing relatively high heat exchange efficiencies. For example, the use of a heat exchange module 1600 in accordance with the present invention results in a pressure drop of about 0.2-0.4 inches of water column in connection with normal breathing, while the pressure drop observed in connection with other heat exchange devices providing a heat exchange efficiency that is comparable to that of a module 1600 in accordance with the present invention is about 2.0-4.0 inches of water column. This factor of ten difference has also been observed at other breathing rates.

In additional embodiments, a heat exchange module 100, 800 or 1600 is used in combination with outdoor equipment or apparel other than head wear or a face mask. For example, a heat exchange module 100, 800 or 1600 may be incorporated in the collar of a jacket, the wall of a tent, or the hood of a sleeping bag. Furthermore, the present invention is not limited to the shapes and configurations of modules discussed in the examples given herein. For instance, modules having any shape may be formed, depending on the particular application or use. Furthermore, modules can be used in combination with other modules. For example, pairs of modules may be used together in a garment or piece of equipment. In addition, although the use of heat exchange elements comprising plastic material have been discussed, the present invention is not so limited. For example, alternate materials such as aluminum or other metals may be used.

The foregoing discussion of the invention has been presented for purposes of illustration and description. Further, the description is not intended to limit the invention to the form disclosed herein. Consequently, variations and modifications commensurate with the above teachings, within the skill and knowledge of the relevant art, are within the scope of the present invention. The embodiments described hereinabove are further intended to explain the best mode presently known of practicing the invention and to enable others skilled in the art to utilize the invention in such or in other embodiments and with various modifications required by their particular application or use of the invention. It is intended that the appended claims be construed to include the alternative embodiments to the extent permitted by the prior art.

What is claimed is:

1. A personal heat exchanger device, comprising:
a plurality of first elements including:
first and second side surfaces; and
a desiccant on at least a one of said side surfaces;
a plurality of second elements including:
first and second side surfaces, wherein each of said first elements is adjacent at least one of said second elements, wherein said second elements further include:
protrusions extending from a substantially planar surface of said first side surface by a first distance; and
protrusions extending from a substantially planar surface of said second side surfaces by said first distance, wherein a distance between said planar side surfaces of each of said first elements and an adjacent side surface of a second element is about equal to said first distance;
an interconnecting member, wherein said first and second elements are positioned spaced apart from and substantially parallel to one another, and wherein said first and second elements are held by said interconnecting member and define at least a first curved surface in a plane that is substantially orthogonal to said first and second side surfaces of said first and second elements.

2. The device of claim 1, wherein at least a first of said protrusions extending from a one of said first and second side surfaces of said second element is in contact with a portion of one of said first and second side surfaces of said first element.

3. The device of claim 1, wherein each of said first and second elements further includes a first edge, and wherein said first edges of said first and second elements define said first curved surface.

4. The device of claim 3, wherein each of said first and second elements further includes a second edge, and wherein said second edges of said first and second elements define a second curved surface.

5. The device of claim 4, wherein said first and second curved surfaces describe an identical curve, wherein said first and second elements are planar, wherein said first curved surface is on a first side of said heat exchanger, and wherein said second curved surface is on a second side of said heat exchanger.

6. A personal heat exchanger device, comprising:
a plurality of first elements including:
first and second side surfaces; and
a desiccant on at least a one of said side surfaces;
a plurality of second elements including:
first and second side surfaces, wherein each of said first elements is adjacent at least one of said second elements, wherein at least some of said plurality of first elements have a length that is different than a length of others of said plurality of first elements;
an interconnecting member, wherein said first and second elements are positioned spaced apart from and substantially parallel to one another, and wherein said first and second elements are held by said interconnecting member and define at least a first curved surface in a plane that is substantially orthogonal to said first and second side surfaces of said first and second elements.

7. The device of claim 6, wherein said at least some of said plurality of second elements have a length that is different than a length of others of said plurality of second elements.

8. The device of claim 6, wherein a first end of each of said plurality of first elements defines a curved perimeter surface.

9. The device of claim 6, wherein said first and second elements comprise substantially planar pieces of material formed from a substantially rigid material.

10. The device of claim 6, wherein said interconnecting member comprises an adhesive.

11. The device of claim 6, wherein said interconnecting member comprises a frame.

12. A personal heat exchanger device, comprising:
a plurality of first elements, each first element including:
first and second side surfaces; and
a desiccant on at least a one of said side surfaces;
a plurality of second elements, each second element including:
first and second side surfaces, wherein each of said first elements is adjacent at least one of said second elements;
an interconnecting member, wherein said first and second elements are positioned spaced apart from and substantially parallel to one another, wherein an open space is maintained between adjacent first and second elements, wherein said interconnecting member comprises a frame, and wherein said frame includes a first channel for receiving a first end of said first and second elements and a second channel for receiving a second end of said first and second elements, and wherein said first and second elements are held by said interconnecting member and define at least a first curved surface in a plane that is substantially orthogonal to said first and second side surfaces of said first and second elements.

13. The device of claim 12, wherein said desiccant of said first element is deposited on at least one of said side surfaces of said first element.

14. The device of claim 12, wherein said second strip of material further includes a desiccant.

15. A personal heat exchanger device, comprising:
a plurality of first elements, each first element including:
   first and second side surfaces; and
   a desiccant on at least a one of said side surfaces;
a plurality of second elements, each second element including:
   first and second side surfaces, wherein each of said first elements is adjacent at least one of said second elements;
an interconnecting member, wherein said first and second elements are positioned spaced apart from and substantially parallel to one another, wherein an open space is maintained between adjacent first and second elements, wherein said interconnecting member comprises a frame, and wherein said frame includes a first channel for receiving a first end of said first and second elements and a second channel for receiving a second end of said first and second elements;
a positioning member operable to position said first and second elements within a respiratory air stream of a user.

16. The device of claim 15, wherein said positioning member comprises a breathing apparatus.

17. A personal respiratory heat exchange module, comprising:
a plurality of heat exchange surfaces, wherein each of said heat exchange surfaces comprises a first edge and a second edge separated from said first edge by an angle;
a curved first module surface formed by said first edges of said heat exchange surfaces, wherein said curved first module surface is concave in at least one plane; and
a curved second module surface formed by said second edges of said heat exchange surfaces;
an interconnecting member, wherein a shape of said curved first module surface is substantially maintained by said interconnecting member, wherein said interconnecting member comprises a frame, wherein said frame includes a first channel operable to receive a first end of said heat exchange surfaces and a second channel operable to receive a second end of said heat exchange surfaces, wherein said first channel includes a first curve corresponding to said curved first module surface, and wherein at least a portion of said first channel includes a second curve corresponding to said curved second module surface.

18. The module of claim 17, wherein said heat exchange surfaces are substantially planar.

19. The module of claim 17, wherein each of said plurality of heat exchange surfaces is substantially parallel to an adjacent heat exchange surface.

20. The module of claim 17, wherein at least some of said heat exchange surfaces comprise a desiccant.

21. The module of claim 17, wherein each of said first and second channels includes a surface that follows said curved first module surface.

22. A personal respiratory heat exchange module, comprising:
a plurality of heat exchange surfaces, wherein each of said heat exchange surfaces comprises a first edge and a second edge;
a curved first module surface formed by said first edges of said heat exchange surfaces;
a curved second module surface formed by said second edges of said heat exchange surfaces; and
an interconnecting member, wherein a shape of said curved first module surface is substantially maintained by said interconnecting member, wherein said interconnecting member comprises a frame, and wherein said frame includes a first channel operable to receive a first end of said heat exchange surfaces and a second channel operable to receive a second end of said heat exchange surfaces, wherein said heat exchange surfaces comprise protrusions operable to space each heat exchange surface from an adjacent heat exchange surface.

23. A personal heat exchange apparatus, comprising:
first means for removing heat and moisture from an exhaled air-stream and for providing heat and moisture to an inhaled air-stream, wherein said first means comprise a rigid, desiccant-coated plastic;
second means for removing heat and moisture from an exhaled air-stream, wherein said second means is parallel to and spaced apart from said first means, wherein said first and second means for removing heat and moisture from an exhaled air stream are fused to one another along at least a first edge of said first and second means for removing heat and moisture from an exhaled air stream;
means for holding end portions of said fused first and second means for removing heat and moisture from an exhaled air stream, wherein said means for holding includes a first channel for receiving said first edge of said first and second means for removing heat and moisture from an exhaled air stream, wherein said means for holding includes a second channel for receiving a second edge of said first and second means for removing heat and moisture from an exhaled air stream, wherein said first edge is opposite of said second edge, and wherein said means for holding defines an open area between said first and second channels though which the exhaled air stream can pass to come into contact with the first and second means for removing heat and moisture.

24. A personal heat exchanger device, comprising:
a plurality of first elements, each first element including:
   at least first and second edges;
   first and second side surfaces; and
   a desiccant on at least a one of said side surfaces;
a plurality of second elements, each second element including:
   at least first and second edges; and
   first and second side surfaces;
an interconnecting member, wherein said first and second elements are positioned spaced apart from and substantially parallel to one another by said interconnecting member, wherein an open space is maintained between at least one first element and at least one second element, wherein said first and second elements are held by said interconnecting member in an untensioned state, and wherein at least said first edges of said plurality of first elements and said first edges of said plurality of second elements define a curve.

25. A personal heat exchanger device, comprising:
a first element including:
   first and second side surfaces; and
   a desiccant on at least a one of said side surfaces;
a second element including:
   first and second side surfaces;
an interconnecting member, wherein said first and second elements are positioned spaced apart from and substantially parallel to one another;
a positioning member operable to position said first and second elements within a respiratory air stream of a user, wherein said positioning member comprises a garment.

* * * * *